United States Patent [19]

Paulson

[11] Patent Number: 5,798,457
[45] Date of Patent: Aug. 25, 1998

[54] CONTINUOUS MONITORING OF REINFORCEMENTS IN STRUCTURES

[75] Inventor: Peter O. Paulson, Calgary, Canada

[73] Assignee: Pure Technologies Inc., Calgary, Canada

[21] Appl. No.: 467,666

[22] Filed: Jun. 6, 1995

Related U.S. Application Data

[63] Continuation-in-part of Ser. No. 436,986, May 8, 1995, abandoned, which is a continuation of Ser. No. 81,878, Jun. 25, 1993, abandoned.

[51] Int. Cl.⁶ ................................................. G01N 29/14
[52] U.S. Cl. .......................................... 73/587; 73/594
[58] Field of Search .............................. 340/566, 690; 364/508, 421; 73/579, 581, 582, 583, 587, 594, 786, 801

[56] References Cited

U.S. PATENT DOCUMENTS

| | | | |
|---|---|---|---|
| 3,702,998 | 11/1972 | Lucas | 340/568 |
| 3,949,353 | 4/1976 | Waters | 340/690 |
| 4,009,463 | 2/1977 | Vercellotti et al. | 340/16 |
| 4,386,343 | 5/1983 | Shiveley | 340/566 |
| 4,408,285 | 10/1983 | Sisson et al. | 364/508 |
| 4,500,979 | 2/1985 | Scott | 73/653 |
| 4,535,629 | 8/1985 | Prine | 73/587 |
| 4,565,964 | 1/1986 | Matthews | 324/51 |
| 4,609,994 | 9/1986 | Bassim et al. | 364/551 |
| 4,644,335 | 2/1987 | Wen | 340/683 |
| 4,649,524 | 3/1987 | Vance | 340/690 |
| 4,738,137 | 4/1988 | Sugg et al. | 73/587 |
| 5,010,503 | 4/1991 | Paton | 73/587 |
| 5,104,391 | 4/1992 | Iugle et al. | 606/11 |
| 5,293,555 | 3/1994 | Anthony | 73/587 |

FOREIGN PATENT DOCUMENTS

| | | |
|---|---|---|
| 8200893 | 3/1982 | Germany. |
| 58-108419 | 6/1983 | Japan. |
| 62-034051 | 2/1987 | Japan. |

OTHER PUBLICATIONS

Muspratt,M.A. "Strain Measurment in Reinforced Concrete Slabs", Jul. 1969, *Strain* pp. 152–156.

Dunn, S.E. et al. "Acoustic Emission Characterization of Corrosion Induced Damage in Reinforced Concrete" Jul. 1984, *Corrosion* pp. 339–343.

Primary Examiner—Christine K. Oda
Attorney, Agent, or Firm—George E. Fisk

[57] ABSTRACT

Method and apparatus for detecting failure of tensioned reinforcements in a structure by means of a plurality of acoustic or seismic detectors disposed about the structure in a known arrangement, processing signals from the detectors to determine frequency contents and origins, and identifying simultaneous signals as due to the failure of tensioned reinforcements in the structure when they meet spectral and origin criteria.

9 Claims, 6 Drawing Sheets

5,798,457

1

CONTINUOUS MONITORING OF REINFORCEMENTS IN STRUCTURES

This application is a continuation-in-part of application Ser. No. 08/436,986, filed May 8, 1995, abandoned, which is a continuation of application Ser. No. 08/081,878, filed Jun. 25, 1993, abandoned.

BACKGROUND OF THE INVENTION

1. Field of the Invention

The present invention is directed to methods and systems for monitoring the integrity of structures and, in particular, to a method and system for monitoring structural reinforcement or securing members, such as post-tensioning cable, in concrete. More particularly still, breakage of such cables is detected, distinguished from background noise, and located by means of subsequent analysis or on a real-time basis. The source of the breakage is located by known triangulation techniques. In addition, cost saving space multiplexing of sensors is used.

2. Related Art

U.S. Pat. No. 3,949,353, granted Apr. 6, 1976 to Waters et al., and titled "Underground Mine Surveillance System", discloses a system for maintaining a continuous log of activity in and around an underground mine where seismic energy in the area is continually monitored, processed and classified into meaningful relative data indications; and which system further includes selectively deployable seismic energy monitoring equipment providing more specific data in the event of mine catastrophe. This system utilizes permanently disposed seismic energy detectors and/or emergency detectors placed in accordance with the particular exigency, and detected seismic energy return is continually processed to maintain a data log indicative of general type and location of mine activity, with particular capability for isolation of unusual seismic events by comparison with statistical data constraints of predetermined character.

U.S. Pat. No. 4,386,343, granted May 31, 1983 to Shiveley, and titled "Acoustic Emission Intruder Alarm System", discloses an acoustic emission burglary detection system for detecting physical attacks made on a protected structure such as a vault, safe or the like. Sensors (13, 14) mounted on the protected structure detect acoustic emission stress wave signals produced by an attack and provide an event signal of a corresponding frequency and with an amplitude and duration dependent upon those of the stress wave signals. Event signals exhibiting a frequency less than 50,000 Hz are much less likely to have been originated by a physical attack upon the protected structure and are filtered out. The remaining event signals which exceed a predetermined level, are integrated over a predetermined time period. If the resulting value exceeds a predetermined level, an alarm is activated. Means are provided for testing the detection circuit by providing electrical pulses through one of the sensors to cause it to generate mechanical stress wave signals in the protected structure which can be detected and processed by the detection circuitry.

U.S. Pat. No. 4,649,524, granted Mar. 10, 1987 to Vance, and titled "Integrated Acoustic Network" discloses an integrated acoustic network system to provide warning of impending groundfall in underground mines. The system includes a plurality of geophones which derive acoustic signals by which the source of seismic disturbances is located, and an array of high frequency piezoelectric sensors which pick up signals from small ground disturbances which precede groundfall. A warning system is provided both at the scene of mining operations and at a central location of impending groundfall and of the location of its occurrence.

In U.S. Pat. No. 3,949,353, unusual seismic events are isolated by comparison with stored statistical data constraints. In U.S. Pat. No. 4,386,343, event signals exhibiting a frequency above 50,000 Hz are integrated over a predetermined time period and, if the resulting value exceeds a predetermined level, an alarm is activated. In U.S. Pat. No. 4,649,524, the number of seismic events is counted and the cumulative amount of energy is estimated for every minute and the ratio of energy/event is calculated.

U.S. Pat. No. 4,535,629, granted Aug. 20, 1985 to Prine, and titled "Method and Apparatus for Structural Monitoring with Acoustic Emission and Using Pattern Recognition", discloses an acoustic emission monitoring system used for monitoring fatigue crack growth in metal or other materials such as occur, for example, in highway bridges during normal traffic loading. The transducers are placed on the plates to be tested to allow detection of acoustic emission from a particular site. By applying specific recognition methods to the acoustic emission AE, detection of flaws can be detected from a random noise background. The pattern recognition technique first subjects the received AE energy to an energy window test and if the energy is within the window, it is subjected to a rate test and if the energy exceeds predetermined rates, it is passed to a location test so as to locate the position of flaws.

U.S. Pat. No. 4,565,964, granted Jan. 21, 1986 to Matthews, et al., and titled "Cable Integrity by Acoustic Emission", discloses a system for monitoring the integrity of a cable, for example a cable following a variable depth sonar body through the ocean. Such a cable comprises a core of electrical wires surrounded by load bearing wires which are secured to the sonar body through a terminator. For various reasons cracks can appear in the load bearing wires and in extreme cases one or more of the wires may break. The monitoring system includes a transducer located near the terminator where the wires are most likely to crack or break. Acoustic emissions caused by the incidence of cracks or breaks are picked up by the transducer. The resulting electrical signals are amplified and passed up the electrical core of the cable to the towing vessel where they are processed. Novel aspects of the system are the water coupling between the location of the cracks or breaks and the transducer and special processing circuitry which enables breaks, cracks and electrical noise to be distinguished from each other.

U.S. Pat. No. 4,738,137, granted Apr. 19, 1988 to Sugg, et al., and titled "Acoustic Emission Frequency Discrimination", discloses an acoustic emission signal processor that selectively sorts acoustic signals on the basis of frequency content, rather than just the frequency. The processor allows rejection of some signals having a particular frequency content, or can provide for separate counting or other processing of these signals.

The above mentioned United States patents are incorporated herein by reference.

SUMMARY OF THE INVENTION

The present invention endeavours to solve the problem of distinguishing and locating a single non-recurring event, namely, the breakage of reinforcing element embedded in concrete. For this reason, neither integrative, cumulative nor statistical techniques of the prior art would work.

Strengthening of concrete structures, such as bridges or concrete floors of modern buildings, is often accomplished by means of highly tensioned cables which are extended through conduits embedded in the concrete. Post-tensioning cables sometimes corrode and break, thereby impairing the integrity of the structure. Often these broken cables remain undetected. The monitoring of these inaccessible structural reinforcements to measure their integrity has long been a problem. Conventionally, the cables are visually inspected involving drilling a view port into the concrete at each cable location. Visual or electrical inspection of the cable is then performed to determine if the cable is still bearing load.

A method and system for monitoring reinforcing elements of a structure nondestructively is provided. Monitoring is performed on a continuous basis by means of acoustic or seismic indicators. When a tensioned reinforcement within a structure breaks, energy, specifically in the form of acoustic and seismic energy, is released into the surroundings. Appropriate detectors responsive to these forms of energy are positioned on or near the structure to detect the energy emissions.

According to a broad aspect of the present invention, a method is provided for monitoring the failure of tensioned reinforcements in a structure comprising: positioning a plurality of acoustic/seismic detectors about the structure in a known arrangement and in close proximity to the structure; processing signals from the detectors; and identifying signals due to the failure of tensioned reinforcements in the structure.

According to a further broad aspect of the present invention there is provided an apparatus for monitoring the failure of tensioned reinforcements in a structure comprising: a plurality of acoustic and/or seismic detectors positioned about the structure in a known arrangement and in close proximity to the structure, means for processing signals from the detectors; and means for identifying signals due to failure of tensioned reinforcements in the structure.

In another method aspect of the present invention, the steps of processing and identifying signals from the detectors further comprise: analyzing signals from the detectors for their frequency content; and identifying the signals as being due to a failure event only at times (i.e. time slices or snapshots) when the frequency content exhibits frequencies above a predetermined frequency-threshold and voltages above a predetermined voltage-threshold.

Accordingly, the method of analysis uses these quantities; frequency, power or energy, and time.

In a further method aspect, the step of processing further comprises converting the signals from the detector to their Fourier transforms.

In a yet further aspect of the present invention, it has been found that rupture of an unbonded post-tensioning strand is identifiable upon detecting a plurality of nearly simultaneous acoustic emissions originating from sources located substantially on a line along the course of the ruptured strand or cable.

This is possible because the speed of sound in the steel cable is faster than the speed of sound in concrete. The rupture of the cable or a wire in the cable produces a sound wave which travels along the length of the cable, and allows several places on the cable to act as a source of energy propagating into the concrete slab.

According to another apparatus aspect of the present invention, there is provided an apparatus for detecting the location of failure of a tensioned reinforcement in a structure comprising: a plurality of detectors positioned about the structure in a known arrangement and in close proximity to the structure, the detectors being responsive to acoustic energy or seismic energy or a combination thereof to produce a signal; central monitoring means coupled to each of the detectors, comprising means for conveying signals from each of the detectors, means for identifying a signal due to failure of the tensioned reinforcement in the structure; timing means for determining the time of arrival of the energy at each of the detectors; and, reporting means to indicate the failure of the tensioned reinforcement.

BRIEF DESCRIPTION OF THE DRAWINGS

The preferred embodiment of the present invention will now be described in detail in conjunction with the annexed drawings, in which.

DETAILED DESCRIPTION OF THE PREFERRED EMBODIMENT

Figure 1:
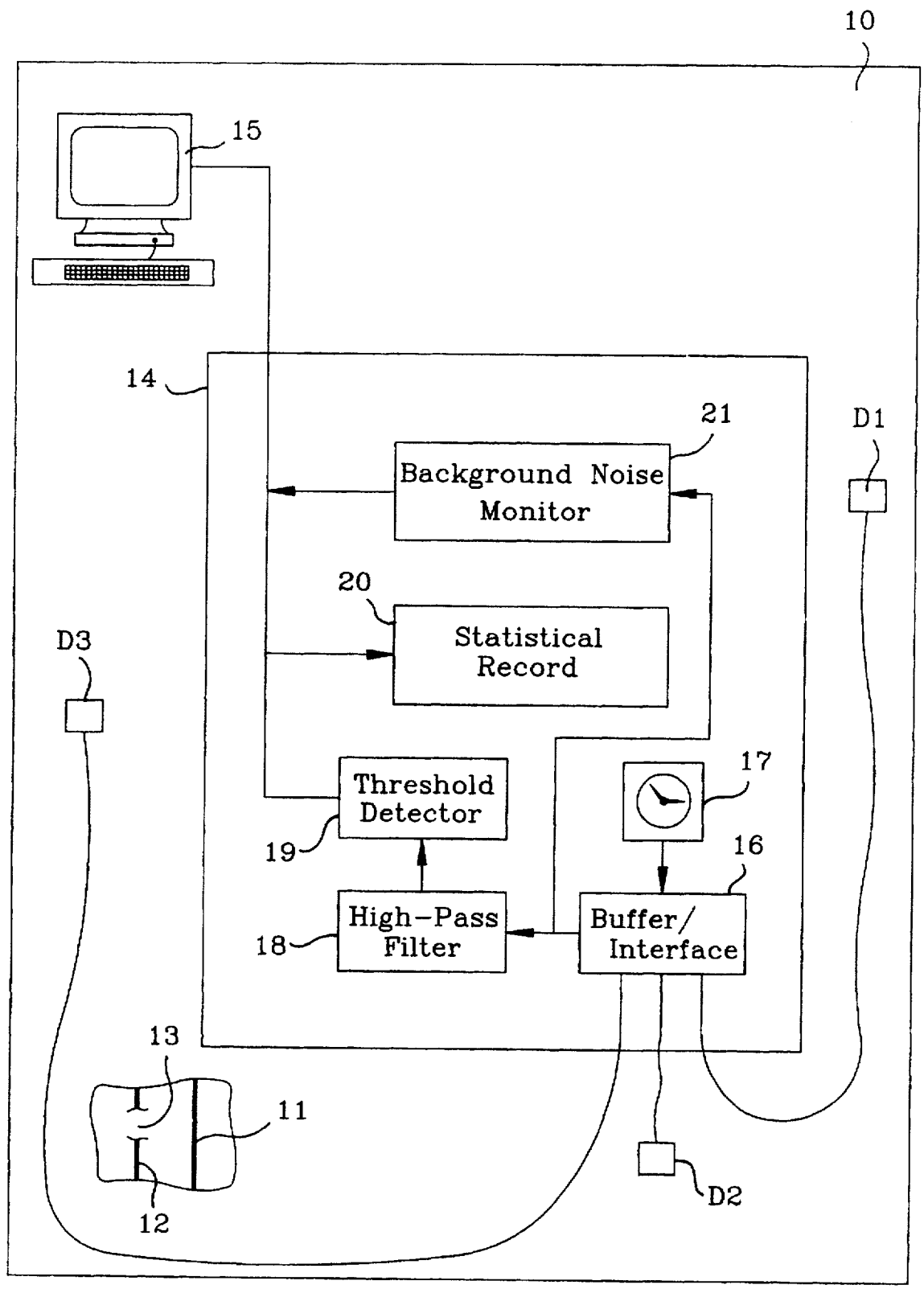
FIG. 1 is an illustrative and block schematic diagram of the system according to the present invention.

Referring to FIG. 1 of the drawings, the system for monitoring the structural integrity of a concrete floor 10 having therein embedded post-tensioning cables 11 and 12, comprises central processor 14, an event record monitor 15, as well as acoustic, seismic or acoustic/seismic sensors or detectors $D_1$, $D_2$ and $D_3$, placed at arbitrary locations close to or contiguous the surface of the floor 10. In the drawing, there is a breakage in cable 12 at 13 which causes signals to be received at detectors $D_1$, $D_2$ and $D_3$. The central processor 14 comprises a buffer and/or interface 16 to which the detectors $D_1$, $D_2$ and $D_3$ are coupled, and which associates signals detected at each of the detectors $D_1$, $D_2$ and $D_3$ with the respective real-time of detection by means of clock 17. The interface 16 multiplexes the signals from the three detectors and applies them to high-pass filter 18 (which may be a filtering routine of the central processor 14) having an approximate cut-off frequency of a few kilohertz, preferably in the present preferred embodiment 6 kHz. The output of the high-pass filter 18 is applied to threshold detector and event identifier 19 which decides, on the basis of the spectral voltage density of the filtered signal, to recognize and identify a breakage event. The processor 14 preferably has capability for keeping a statistical record 20, which would be used to aid in predicting future failures. A background noise monitor 21 preferably continuously monitors the background noise detected by the detectors $D_1$, $D_2$ and $D_3$ and sounds or displays an alarm on the monitor 15 should the background noise level fall below a preselected value. Thus, the noise monitor 21 receives its input signal prior to filtering and processing.

Figure 2:
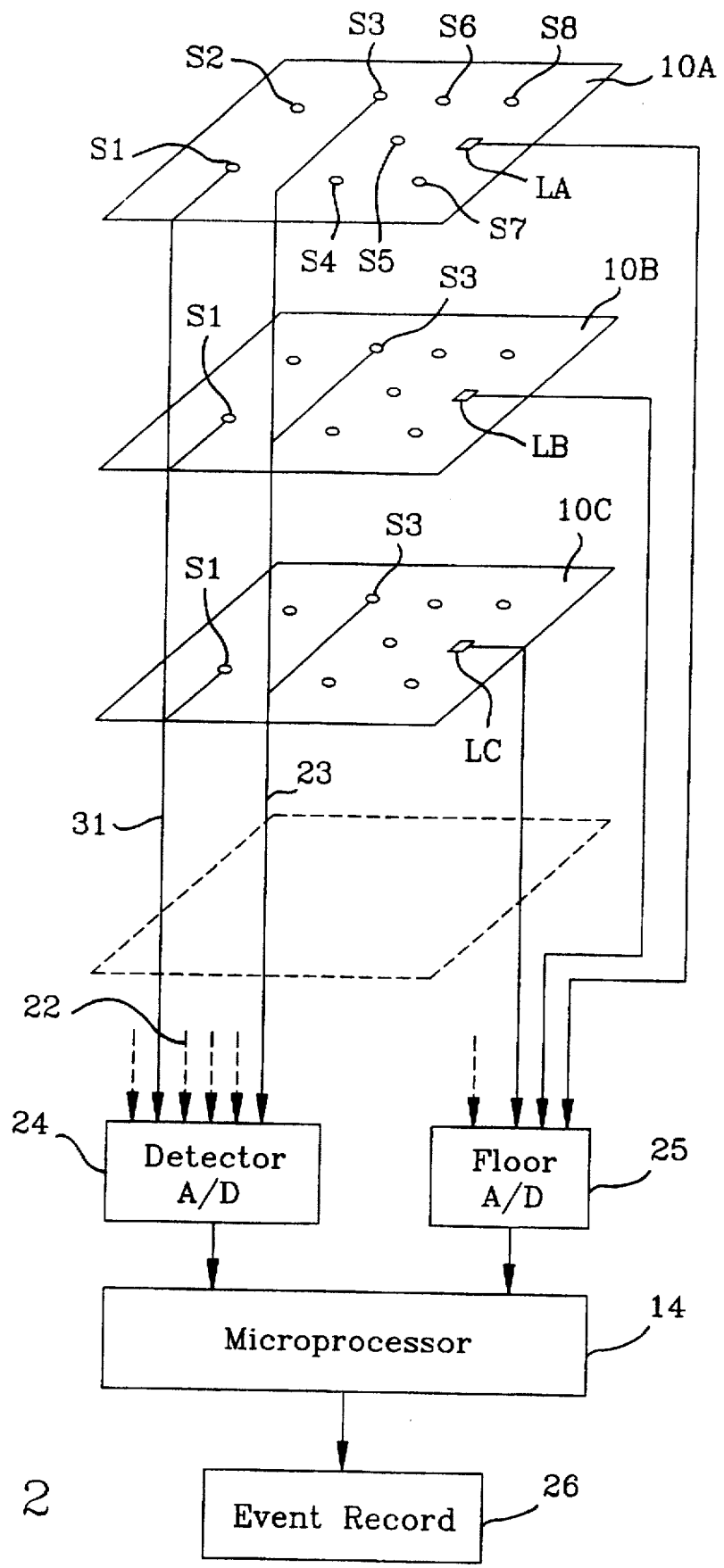
FIG. 2 illustrates an embodiment of the present invention for multi-floored structure.

Referring now to FIG. 2, this shows an embodiment suitable for a multi-floor structure, comprising a plurality of floors, of which three are shown 10A, 10B and 10C. Each floor has a number of sensors\detectors S1 to S8 and a floor detector LA, LB, LC, etc. In order to reduce cost and wiring complexity, and given the very small likelihood of simultaneous cable breakage, the detectors are spatially multiplexed. As shown in FIG. 2, all detectors S1 (one on each floor) may be at the same respective position for ease of installation and analysis (but they need not be as long as their positions are known). All detectors S1 are connected in parallel to a bus 31, all detectors S2 are connected to bus 22, (not shown), all detectors S3 are connected to a bus 23, and so forth. Preferably, the detectors have high impendence outputs, in order not to represent a significant load to each other. Each floor is identifiable by a detector LA, LB, LC etc. The outputs of the sensors S1 to S8 are applied via the respective buses 31, 22, 23 etc. to a detector A/D (analog-to-digital) converter 24, while the outputs of the floor detectors, LA, LB, LC etc. are applied to a floor A/D converter 25, the function of the latter being simply to identify the floor in which a failure event occurs, but not the location of the breakage on the floor, which is accomplished by triangulation by means of the sensors S1 to S8 in the particular floor. The multiplexed output signals from the A/Ds 24 and 25 are applied to the processor 14, which keeps track of the events in real-time and outputs the event record 26.

Figure 3:
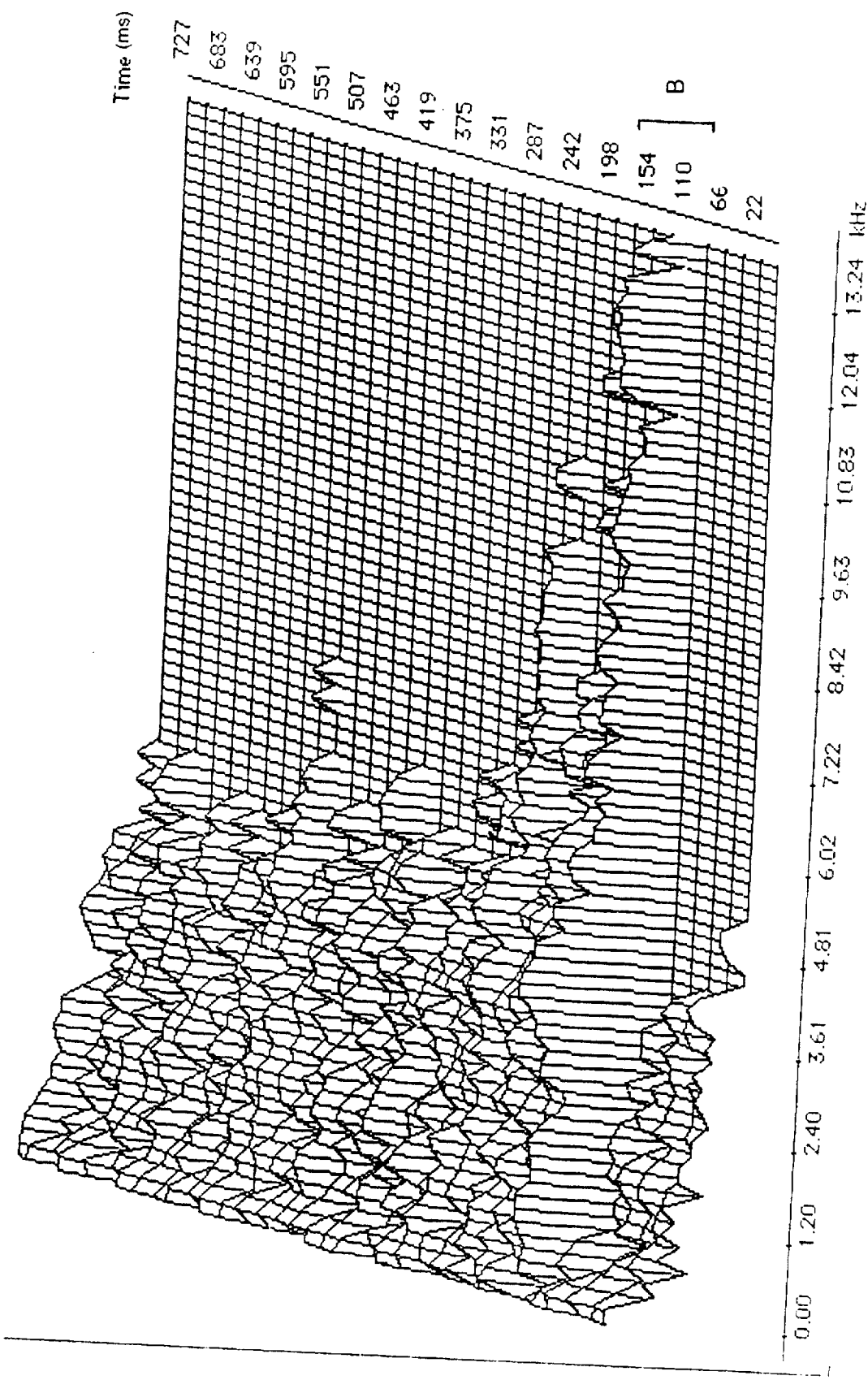
FIG. 3 shows an example Fourier transform showing the frequency spectrum from one of the detectors shown in FIGS. 1 and 2.

It was mentioned in conjunction with FIG. 1, that instead of using a high-pass filter 18 a software filtering routine may be used. While there are several methods of identifying valid failure signals, a preferred method is to use the Fourier transform of the detector signals. The Fourier transform is the conversion of signals which are time-varying voltage functions from detectors to frequency dependent voltage (or power) density functions. This is a well-known operation in signal processing, but has been found to be particularly useful in the noisy operating environment of the present system. FIG. 3 of the drawings shows a graphic illustration of such Fourier transform of an actual detector signal at the time of an exemplary experiment (described under Example 1, infra). The graph shows the spectral distribution of detector voltage levels versus time. As may be seen, there is clear spectral presence between approximately 6 kHz and 13 kHz in the period between approximately 60 ms and 200 ms after the record commenced. Thus, the background noise monitor 21 continuously indicates system sanity while the spectral components do not appreciably exceed the 6 kHz threshold. The system detects a breakage event once the spectral profile exhibits the characteristics shown in FIG. 3, even if only for milliseconds.

EXAMPLE 1

With reference to FIGS. 1 and 3, in an experimental embodiment of the invention the three piezoelectric detectors $D_1$, $D_2$ and $D_3$ (model 273-065A, manufactured by the Archer Company) were placed on the surface of a 30 m×15 m slab of 20 cm thick concrete which formed one floor of a parking garage (not in use and closed to the public) in Lethbridge, Alberta. The floor had been reinforced when constructed with post-tensioned steel cables. The detectors $D_1$, $D_2$ and $D_3$ were placed in a triangular array. A microprocessor was connected by conventional wiring to the three detectors. The detectors were arranged to record seismic waves passing through the concrete floor. The garage, which was slated for demolition, was known to have reinforcing cables in an advanced state of corrosion. One such cable was exposed, and breakage was induced. FIG. 3 is the Fourier Transform graph showing the effect of this breakage. The ordinate of the graph shows time after commencement of recording (in milliseconds) and the abscissa shows recorded frequency in kHertz. The vertical direction represents the amplitude of detected signals in millivolts. The graph is a record of the output of one of the detectors. It will be evident that, prior to approximately 88 milliseconds, signals of relatively low amplitude and a frequency under about 7 kHz were recorded. These represent background noise, such as traffic passing, movement within the parking garage, etc. At 88 milliseconds, the induced cable breakage was detected. This caused signals to be generated at frequencies as high as 13 kHz and above. Higher than background noise frequencies occurred until approximately 160 milliseconds on the measuring scale. Similar patterns were recorded by the two other detectors.

EXAMPLE 2

Figure 4A:
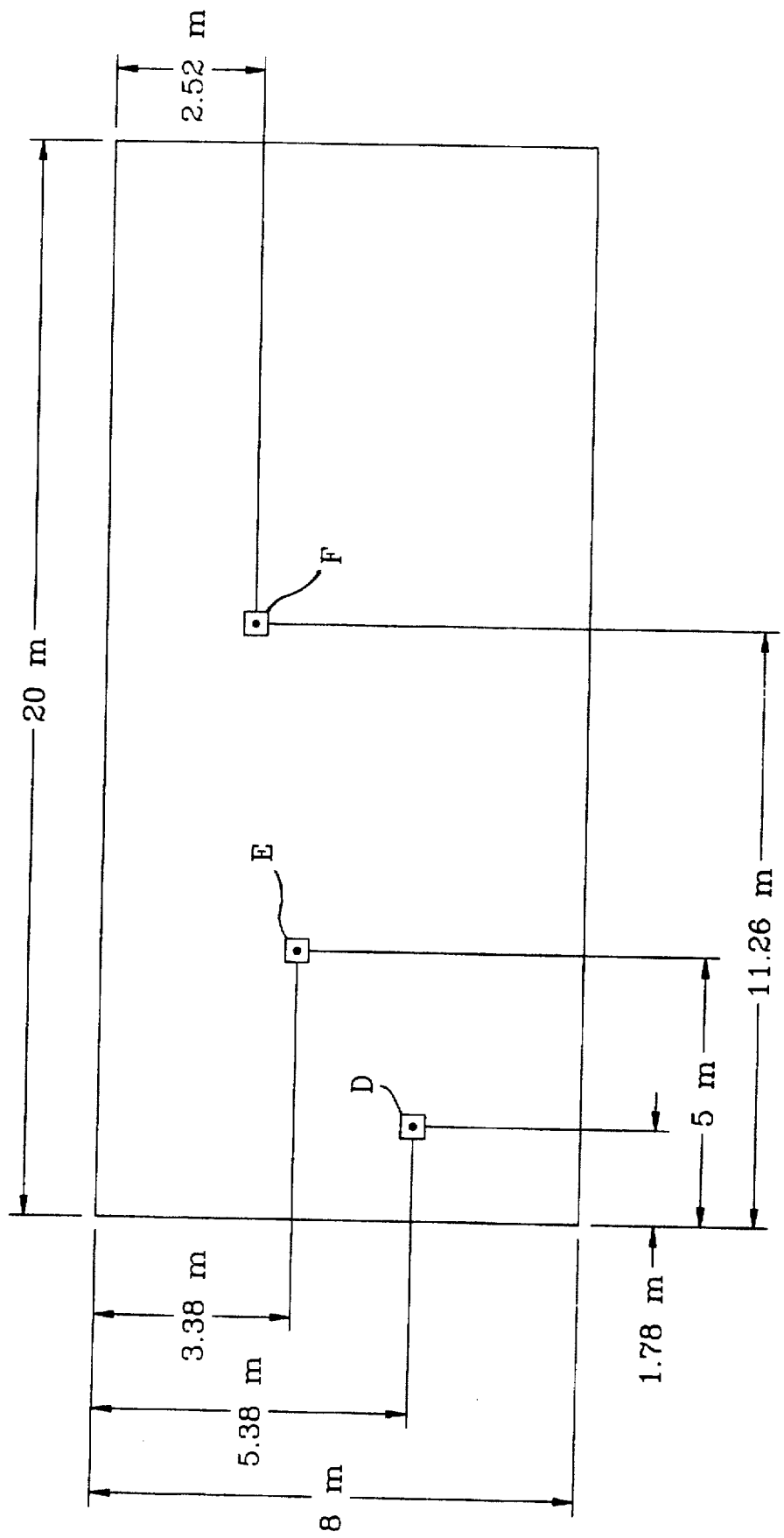
FIGS. 4A and 4B are illustrations useful in explaining operation of the present invention.
Figure 4B:
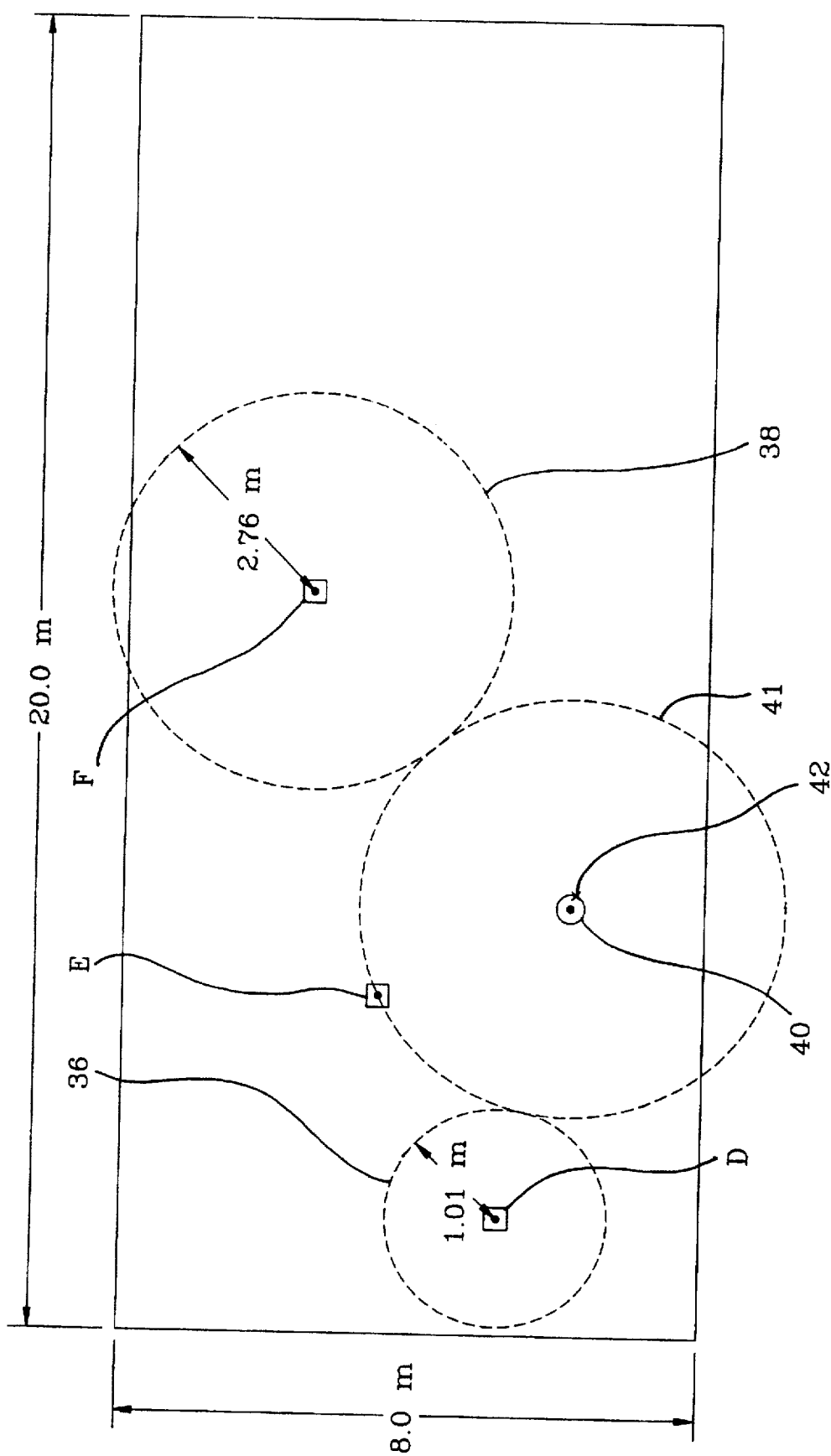

With reference to FIGS. 4A and 4B, in a second example, directed to demonstrate the failure locating feature of the invention, a failure event was simulated by dropping a 1 kg weight from a height of 30 cm onto a randomly selected location 40 on a concrete slab floor of an office building in Calgary, Alberta (closed to the public). The portion of floor studied measured 8.0 m×20.0 m. Three piezoelectric detectors, of the type used in Example 1 identified as D, E and F, were located as shown in FIG. 4A. The initial burst of high amplitude and high frequency waves following the simulated failure was found to arrive at detector E first. The waves arrived at detector D 0.7 milliseconds later and then at detector F 1.2 milliseconds after the first waves had reached detector E. With reference to FIG. 4B, the known locations of the detectors and the relative differences in arrival times can be used to find the location of the break. To locate origin, the locations of sensors D, E and F are plotted on a graph representative of the slab. Using the relative arrival times delays and the velocity of the seismic energy through the structure (found to be 2400 m/s), the comparative distances from origin when compared to detector E are determined as follows:

Sensor D delay =0.7 ms

Additional distance from origin as compared to sensor E

=0.7 ms×2400 m/s

=1.61 m and,

Sensor F delay =1.2 ms

Additional distance from origin as compared to sensor E

=1.2 ms×2400 m/s

=2.76 m.

These distance values are used as radii for the drafting of circles about their respective sensor as is shown in phantom at 36 and 38. A circle 41, shown in phantom, is then drawn to intersect sensor E and to contact both circle 36 about sensor D and circle 38 about sensor F. In this way the origin is determined to be the center 42 of circle 41. The actual origin was, in this embodiment, found to be as indicated at 40. This was of course known, as the simulated breakage had been induced. The actual origin compared very closely with the calculated origin, indicating an error of 0.23 m.

While the above embodiment uses only seismic detection, both seismic and acoustic detection may be used. Where both forms are used only two detectors need be used to locate origin. Reflections of energy may also be used to pin-point origin, however this requires precise locating of reflective structures. Further, while the arrival of the first wave pattern is clearly recognizable reflective wave patterns are very complex.

Figure 5:
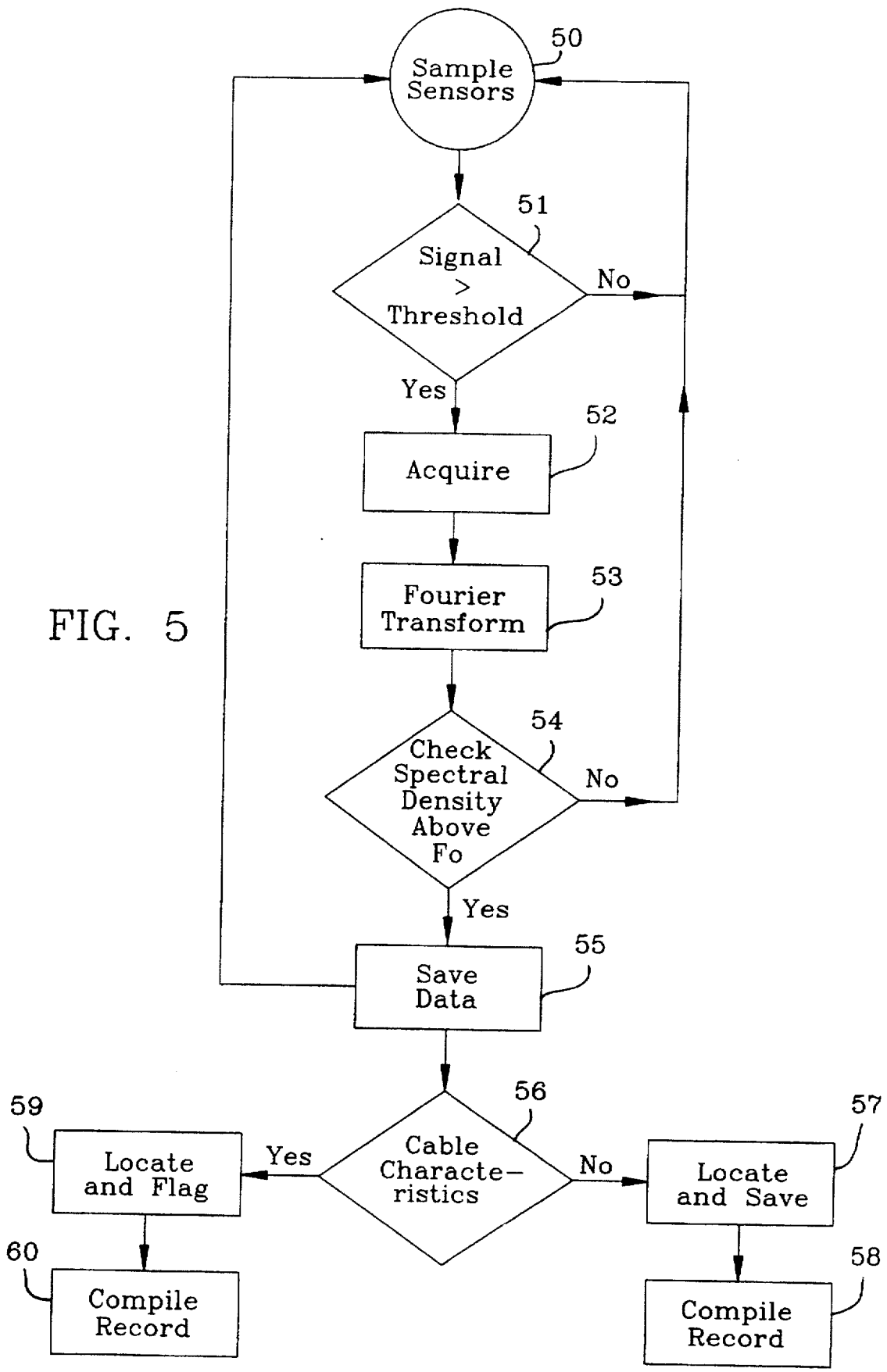
FIG. 5 is a flow chart useful in explaining operation of the system of FIGS. 1 and 2.

Referring now to FIG. 5 of the drawings, the operation of the system shown in FIGS. 1 and 2 is described. The system continuously samples the sensors (50) and once a signal from any sensor exceeds the background noise threshold (51), it acquires the signal from all sensors (52) and performs a Fourier transform operation thereon (53), whereupon the spectral density of the frequencies obtained from such transformation is examined (54), and the system saves the data (55), otherwise it returns to the sampling routine (50). The data saved in step (55) is then analyzed (56), for example, to find if it matches the cable characteristics as shown in FIG. 3. If it does not match, then the event is located and saved (57) (once all sensor data is in) and a record is compiled (58). If it does match then the cable breakage event is located and flagged (59), and, of course, a record is also compiled (60).

While the present invention is described using, as an exemplary embodiment, the monitoring of post-tensioning cables in a concrete structure, the invention can equally be applied to monitoring other tensioned structural reinforcements or securing members where, for example, the reinforcements or securing members are subject to breakage. Thus the present invention may be used to monitor structures including suspension bridge wires; rivets or skin in airplanes; bolted structures; bonded cables in bridges; ship hulls and bulkhead; bolted structures such as cranes or towers; bonded cables cast adhesively in concrete; anchoring cables and tiebacks. Preferably three or more detectors are positioned about the structure. Three detectors allow the origin of energy emissions to be located quickly without employing an excessive number of detectors. The number of detectors employed is dependent on, for example, the expected amount of energy released during the event and the sensitivity of the detectors.

The detectors are responsive to acoustic energy and/or seismic energy. Suitable detectors for use in the present invention include piezoelectric transducers,capacitive transducers, accelerometers, microphones of all types, inductive systems such as geophones, audio-acoustic transducers, acousto-optical transducers, magnetic inductive devices or optical devices. Many of the detectors respond only to one of acoustic energy or seismic energy. However, a piezoelectric transducer responds to both. Most accelerometers do not respond well to acoustic emissions but do respond to seismic emissions. Accelerometers may be linked to diaphragms to increase their acoustic sensitivity. Optical detective devices such as acousto-optical transducers or optical accelerometers use a wide variety of methods to convert strain and stress into a change in the optical properties of a device, including the use of fibre optics or intensity variations. Optical devices can be sensitive to both acoustic and seismic emissions. An example of a suitable detector is the Lars 100 interferometer of Gradient Lens Corp.

The detectors are positioned in close proximity to the structure and preferably in contact with the structure. The detectors can be embedded in the concrete of a bridge or floor slab. However, to enhance the usefulness and simplicity of the apparatus, it is preferred that the detectors remain on the surface of the structure. In this way the detectors may detect air-borne acoustic energy as well as structure-borne acoustic energy arising from the event to be detected such as a cable failure. However, because of the slow velocity of air-borne acoustic emissions when compared to those of structure-borne and seismic emissions, air-borne acoustic energy is not of particular interest in the preferred embodiment of the present invention. As an example, the velocity of air-borne acoustic energy is 300 m/s while acoustic and seismic concrete-borne energy pressure wave and shear wave velocities are approximately 5000 m/s and 2300 m/s, respectively, but, of course, knowing the exact velocity of propagation is not necessary. The compression of concrete may cause variances in the velocities, so tests may be carried out to determine the acoustic and/or seismic velocity (depending on which is used in the particular installation) in the concrete of the structure if the velocity information is to be used to locate the site of the failure.

In response to the detection of an energy wave each detector produces a signal. The detectors may collect the signal data independently, on some appropriate collecting means such as magnetic tapes, until the information is required. When required, the collected data is analyzed to recognize a signal relating to reinforcement failure. Preferably, however, the detectors are coupled to the central processor 14 allowing continuous monitoring of the detectors.

When both acoustic and seismic responsive detectors are used, the time of arrival of energy of both forms may be recorded independently and compared to pin-point the origin. Employing detectors which are responsive to more than one form of energy is beneficial in finding origin as well as recognizing a cable failure at times when there is excessive background noise in one of the energy forms. If there should be excessive background noise in one energy form, the other forms may be used to provide signals which are not distorted.

It will be understood that the forgoing description of the invention is by way of example only, and variations will be evident to those skilled in the art without departing from the scope of the invention, which is as set out in the appended claims.

What is claimed is:

1. A method for monitoring the failure of tensioned reinforcements in a structure comprising the steps of:

(a) positioning a plurality of acoustic or seismic detectors about the structure in a known arrangement and in close proximity to the structure;

(b) processing signals from the detectors;

(c) identifying those of said signals which are due to the failure of a tensioned reinforcement in the structure;

(d) identifying at least one signal received at more than two sensors after passage from an origin through a medium to such sensors;

(e) determining the relative times of arrival of said identified signal at more than two sensors;

(f) calculating the origin of said identified signal from the difference of its time of arrival at each of said more than two sensors.

2. The method as claimed in claim 1, wherein the steps of processing and identifying those of said signals which are due to failure of a tensioned reinforcement further comprise: analyzing said signals from the detectors for frequency contents; and indentifying said signals as being due to failure of a tensioned reinforcement only when the frequency content of said signals exhibits frequencies above a predetermined frequency-threshold and voltages above a predetermined voltage-threshold.

3. The method as claimed in claim 1, wherein the step of processing further comprises: converting the signals from the detectors by Fourier transforms.

4. The method as claimed in claim 3, wherein said signals are identified as being due to the failure of a tensioned reinforcement in the structure if such signals are a plurality of nearly simultaneous acoustic emissions originating from sources located substantially on a line along a tensioned reinforcememt cable.

5. The method as claimed in claim 1, wherein said signals are identified as being due to the failure of a tensioned reinforcement in the structure if such signals are a plurality of nearly simultaneous acoustic emissions originating from sources located substantially on a line along a tensioned reinforcement cable.

6. The method as claimed in claim 1, wherein a said signal is identified as being due to the failure of tensioned reinforcement in a structure when it exhibits a short burst having spectral components at frequencies greater than 6 kHz.

7. A method as claimed in claim 1, in which said detectors are placed in contact with the structure.

8. A method as claimed in claim 1, in which said signals are acoustic signals.

9. A method as claimed in claim 1, in which said signals are seismic signals.

* * * * *